United States Patent
Anilovich et al.

(10) Patent No.: US 6,957,562 B2
(45) Date of Patent: Oct. 25, 2005

(54) PASSIVE OXYGEN SENSOR DIAGNOSTIC

(75) Inventors: Igor Anilovich, Walled Lake, MI (US); Thomas L. Ting, Troy, MI (US)

(73) Assignee: General Motors Corporation, Detroit, MI (US)

(*) Notice: Subject to any disclaimer, the term of this patent is extended or adjusted under 35 U.S.C. 154(b) by 98 days.

(21) Appl. No.: 10/624,737

(22) Filed: Jul. 22, 2003

(65) Prior Publication Data

US 2005/0016253 A1 Jan. 27, 2005

(51) Int. Cl.[7] .......................................... G01N 27/00
(52) U.S. Cl. ........................................................ 73/1.06
(58) Field of Search ............................... 73/1.06, 23.32, 73/23.33, 31.06; 204/401

(56) References Cited

U.S. PATENT DOCUMENTS

| | | | | |
|---|---|---|---|---|
| 4,241,710 A | * | 12/1980 | Peterson et al. | 123/680 |
| 4,981,125 A | * | 1/1991 | Kato et al. | 123/693 |
| 5,227,975 A | * | 7/1993 | Nakaniwa | 701/103 |
| 5,431,011 A | * | 7/1995 | Casarella et al. | 60/274 |
| 5,514,968 A | * | 5/1996 | Spanjers | 205/782.5 |
| 5,558,752 A | * | 9/1996 | Wang et al. | 204/401 |
| 5,801,295 A | | 9/1998 | Davey et al. | 73/1.06 |
| 6,200,443 B1 | * | 3/2001 | Shen et al. | 204/401 |

* cited by examiner

Primary Examiner—Charles Garber
(74) Attorney, Agent, or Firm—Christopher DeVries

(57) ABSTRACT

An engine exhaust sensor diagnostic system includes an oxygen sensor and a controller. The controller monitors a signal generated by the oxygen sensor, determines a rate of change of the signal, and computes diagnostic parameters. The controller indicates malfunction of the oxygen sensor if the diagnostic parameters are smaller in magnitude than corresponding thresholds.

15 Claims, 4 Drawing Sheets

PASSIVE OXYGEN SENSOR DIAGNOSTIC

FIELD OF THE INVENTION

The present invention relates to diagnostic systems for vehicles, and more particularly to a passive inlet oxygen sensor diagnostic.

BACKGROUND OF THE INVENTION

During the combustion process, gasoline is oxidized and hydrogen (H) and carbon (C) combine with air. Various chemical compounds are formed including carbon dioxide ($CO_2$), water ($H_2O$), carbon monoxide (CO), nitrogen oxides ($NO_x$), unburned hydrocarbons (HC), sulfur oxides ($SO_x$), and other compounds.

Automobile exhaust systems include a catalytic converter that reduces exhaust emissions by chemically converting the exhaust gas into carbon dioxide ($CO_2$), nitrogen (N), and water ($H_2O$). Exhaust gas oxygen sensors generate signals indicating the oxygen content of the exhaust gas. An inlet oxygen sensor monitors the oxygen level associated with an inlet exhaust stream of the catalytic converter. This inlet $O_2$ sensor is also the primary feedback mechanism that maintains the air-to-fuel (A/F) ratio of the engine at the chemically correct or stoichiometric A/F ratio that is needed to support the catalytic conversion processes.

Oxygen ($O_2$) sensors are categorized as either narrow range or wide range. The terms narrow and wide refer to the size of the A/F window that the $O_2$ sensor varies in an analog fashion. Narrow range exhaust stream $O_2$ sensors are sometimes referred to as "switching" sensors. These sensors transition between lean and rich sensor signals in a narrow A/F ratio range that brackets the stoichiometric A/F ratio.

System diagnostics require properly functioning oxygen sensors. Therefore, the oxygen sensors are periodically checked to ensure proper function. Traditionally, intrusive checks are employed to check the operation of the sensors. During the intrusive checks, the A/F ratio is manipulated and the sensor response is monitored. However, these intrusive checks may increase exhaust emissions and/or cause engine instability and reduced driveability that may be noticeable by a vehicle operator.

SUMMARY OF THE INVENTION

Accordingly, the present invention provides an engine exhaust sensor diagnostic system that includes an oxygen sensor and a controller. The controller monitors an oxygen signal generated by the oxygen sensor and determines a rate of change of the oxygen signal. This rate of change is used to compute diagnostic parameters, which are highly sensitive to sensor malfunction. The controller indicates malfunction of the oxygen sensor if, for example, diagnostic parameters are below thresholds. In general, a multivariable pair of diagnostic parameters can be used for diagnostic decision resulting from a joint assessment of the parameter values against two dimensional thresholds.

In one feature, the controller indicates proper function of the oxygen sensor if the diagnostic parameters are above corresponding thresholds.

In another feature, the controller classifies the rate of change into one of a positive class, a negative class and an excluded class. The excluded class rate of change is ignored. The positive class diagnostic parameters are compared to the positive thresholds and the negative class diagnostic parameters are compared to the negative thresholds. The controller indicates a positive class malfunction if the positive class diagnostic parameters are below the positive thresholds and indicates a negative class malfunction if the negative class diagnostic parameters are above the negative thresholds. The controller indicates proper positive class function if the positive class diagnostic parameters are above the positive thresholds and indicates proper negative class function if the negative class diagnostic parameters are below the negative thresholds.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
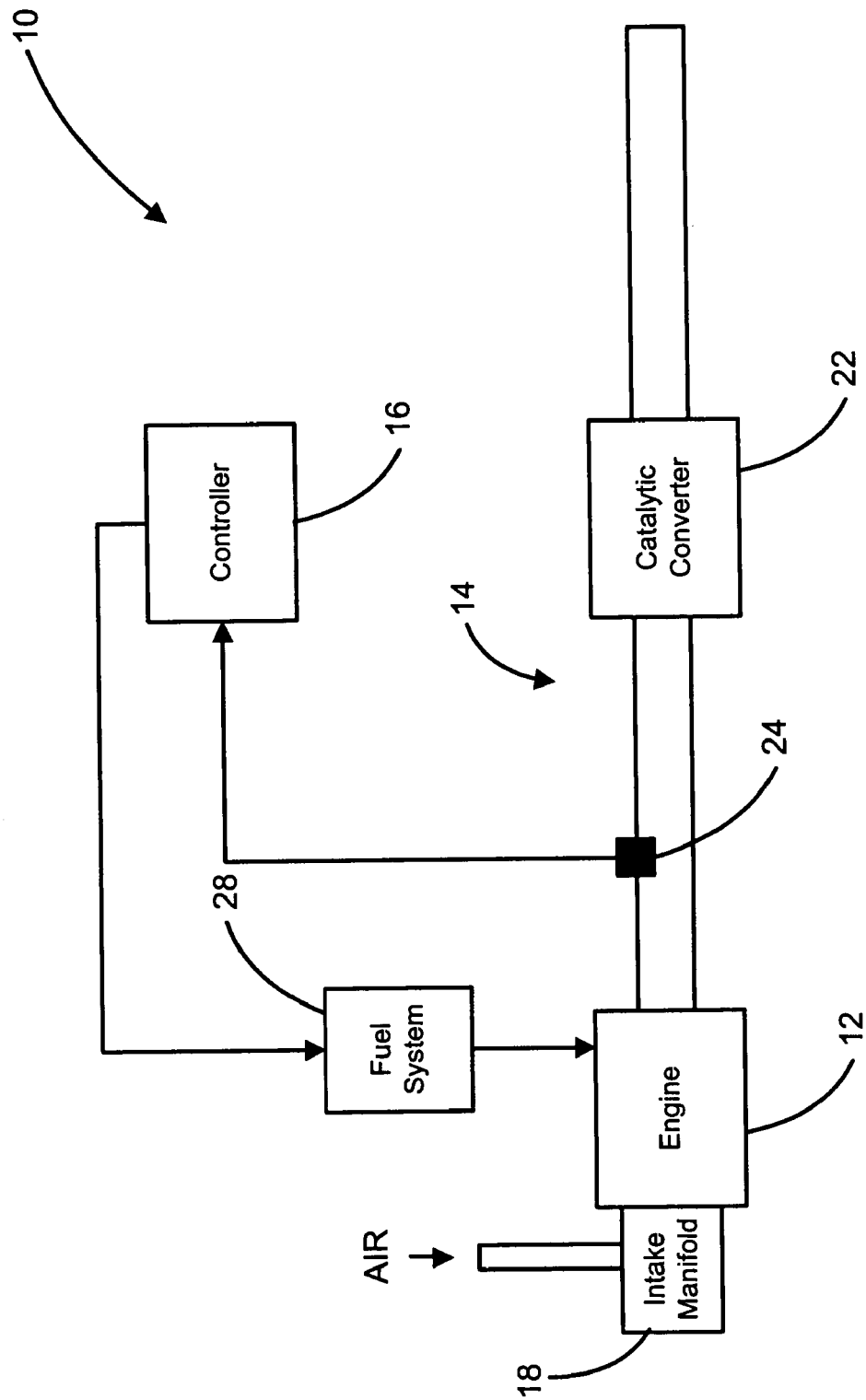
FIG. 1 is a functional block diagram of an engine system including a controller that performs a passive oxygen sensor diagnostic according to the present invention.

The following description of the preferred embodiment is merely exemplary in nature and is in no way intended to limit the invention, its application, or uses. For purposes of clarity, the same reference numbers will be used in the drawings to identify similar elements.

Referring now to FIG. 1, an engine system 10 includes an engine 12, an exhaust system 14 and a controller 16. Air is drawn into the engine through an intake manifold 18 and is combusted with fuel inside the engine 12. The gases produced through combustion exit the engine through the exhaust system 14. The exhaust system 14 includes a catalytic converter 22, and a pre-catalyst or inlet oxygen sensor 24. The exhaust gases are treated within the catalytic converter 22 and are exhausted to the atmosphere.

The inlet oxygen sensor 24 generates an oxygen signal that is communicated to the controller 16. The inlet oxygen sensor 24 provides an inlet A/F ratio signal. The controller 16 communicates with a fuel system 28 to regulate fuel flow to the engine 12. In this manner, the controller 16 regulates the A/F ratio of the engine 12.

Figure 2:
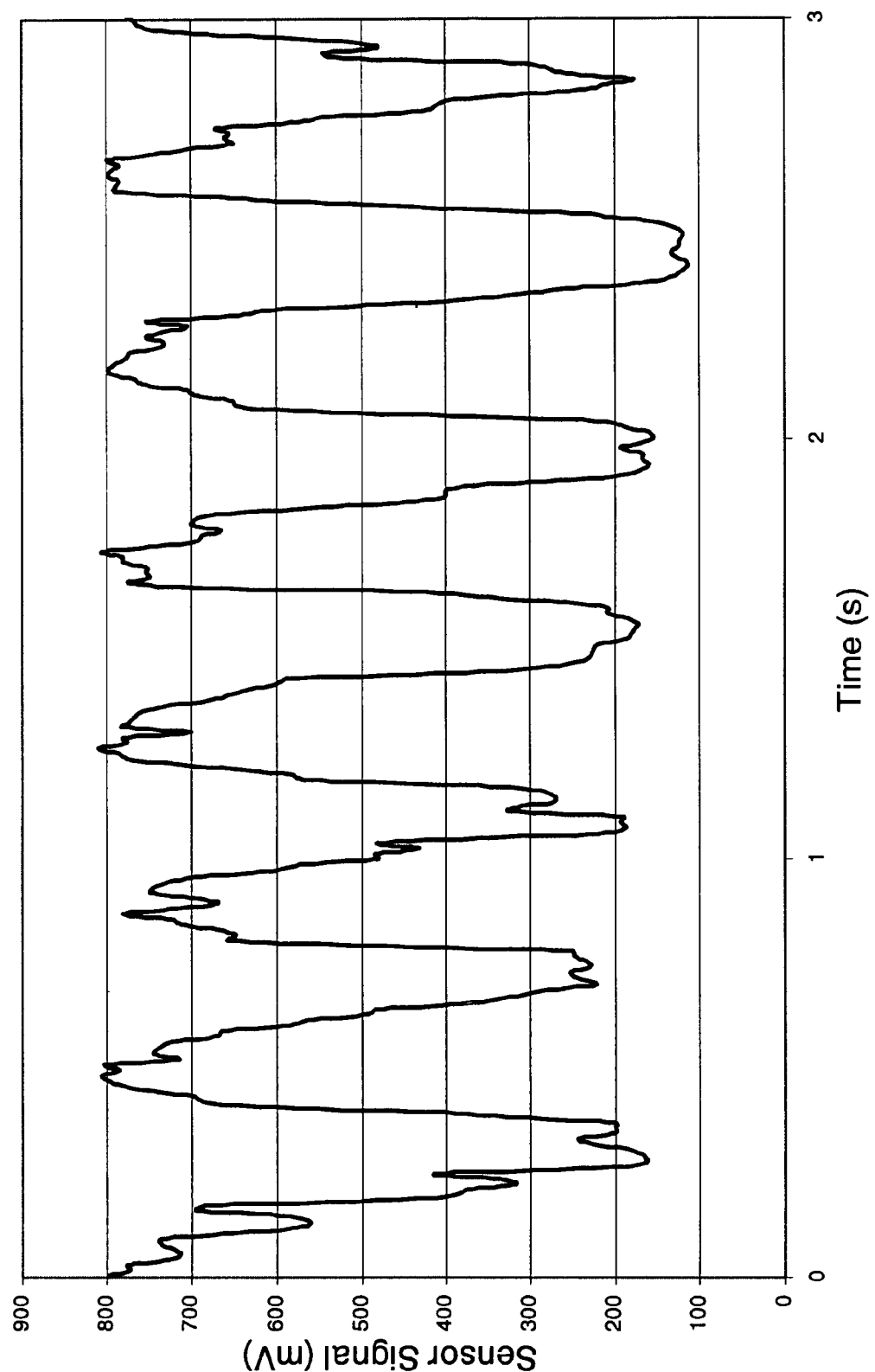
FIG. 2 is a graph illustrating a signal generated by a healthy oxygen sensor.
Figure 3:
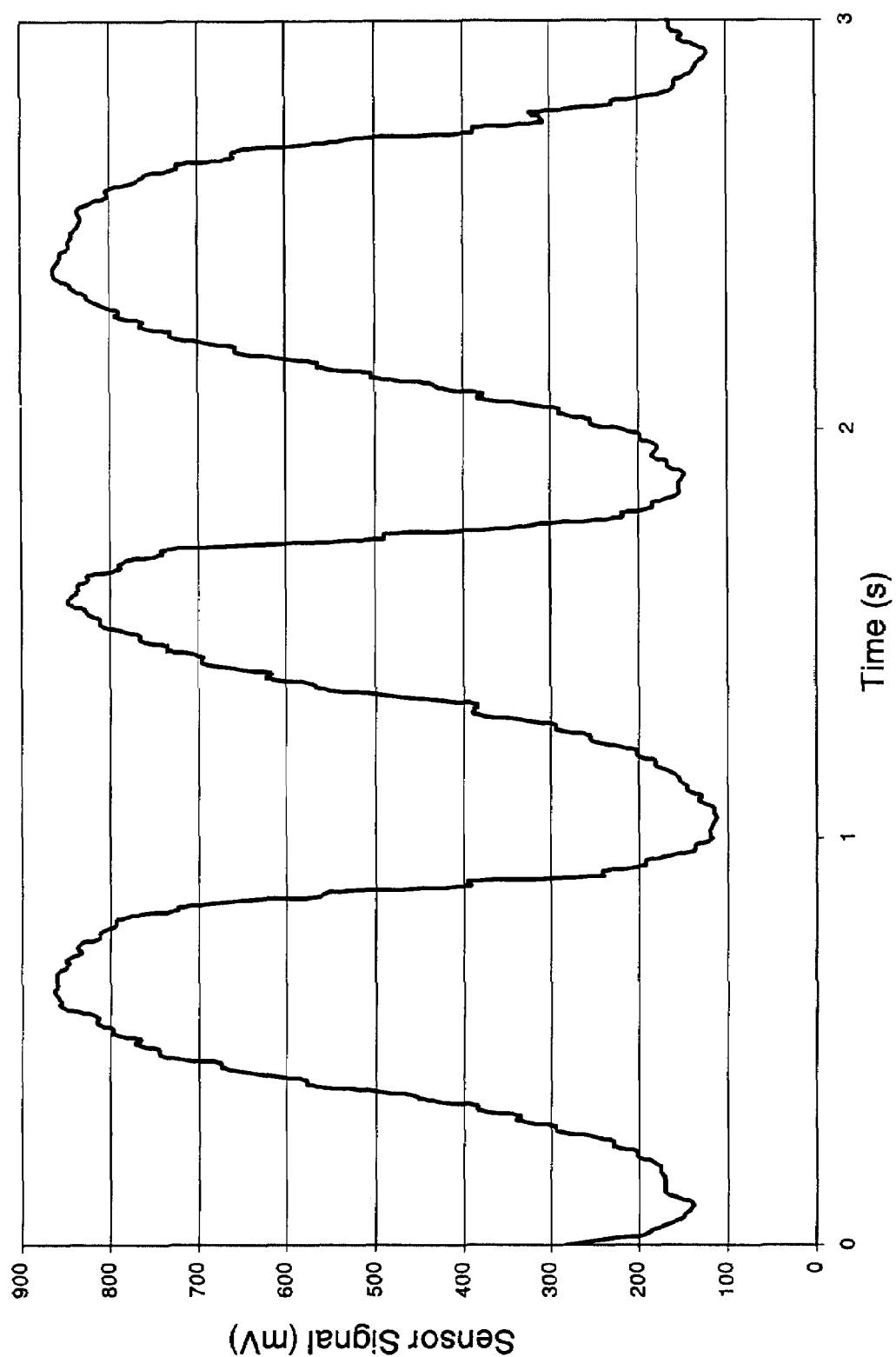
FIG. 3 is a graph illustrating a signal generated by a malfunctioning oxygen sensor.

Referring now to FIGS. 2 and 3, the inlet oxygen sensor 24 is typically a narrow range "switching" sensor. The voltage output signal is generated by the sensor based on the oxygen content of the exhaust gases passing the sensor 24 relative to stoichiometry. This signals a transition between lean and rich in a narrow A/F ratio range that brackets the stoichiometric A/F ratio. As best seen in FIG. 2, an oxygen sensor signal generated by a healthy or operating sensor oscillates back and forth between rich and lean values at a relatively constant frequency. The most common characteristic of a malfunctioning oxygen sensor is a lazy or sluggish response, as best seen in FIG. 3. For a malfunctioning oxygen sensor, an increased amount of time is required to complete the transition from rich to lean and/or lean to rich.

The passive oxygen sensor diagnostic of the present invention monitors the performance of the inlet oxygen sensor 24 by determining the slope of the sensor signal. For any given time point, the instantaneous rate of change of the sensor signal is determined by calculating the ratio of differences between a current and a prior sensor signal and the current and prior time points.

The rate of change is classified in one of three classes: a positive rate class, a negative rate class and an excluded rate class. The positive rate class includes rates of change corresponding to positive slopes (i.e., transition from lean to rich). The negative rate class includes rates of change corresponding to negative slopes (i.e., transitions from rich to lean). The excluded rate class includes rates of change corresponding to near zero slopes (i.e., the troughs and crests of the signal wave form). The rates of change in the excluded rate class generally include low positive or negative rates and are ignored by the diagnostic. The excluded rate class information is ignored to prevent dilution of the information contained in the true signal transition period. In general, if the absolute value of the currently determined rate is below an exclusion limit (i.e., the rate of change is too slow), the corresponding data point is classified to be in the excluded rate class.

The diagnostic monitors the instantaneous rates over a predetermined period and records the rates in the three bins. The diagnostic processes the positive and negative rate classes to provide diagnostic parameters for evaluating the performance of the oxygen sensor. The rates can be processed in a number of manners to generate diagnostic parameters, which indicate whether or not a sensor is healthy. For example, an average of the positive rates ($P_{RATEAVG}$) or negative rates ($N_{RATEAVG}$) can be used as diagnostic parameters. To evaluate the transition performance of a particular sensor, these averages are respectively compared to positive and negative thresholds. If the particular average is larger than or equal in magnitude to its respective threshold, the sensor is deemed to be functioning properly. If the average is smaller in magnitude than its respective threshold, the signal response is sluggish and the sensor is deemed to be malfunctioning. It is anticipated, however, that other methods can be used to compute the diagnostic parameters, such as determining a rate variance or a weighted moving average and comparing these values to respective predetermined thresholds. Still other functions will be apparent to skilled artisans. In addition, supplemental tests can be used to further clarify the operation of the sensor. For example, additional tests can be used to identify a sensor that is going bad before the sensor fails.

Figure 4:
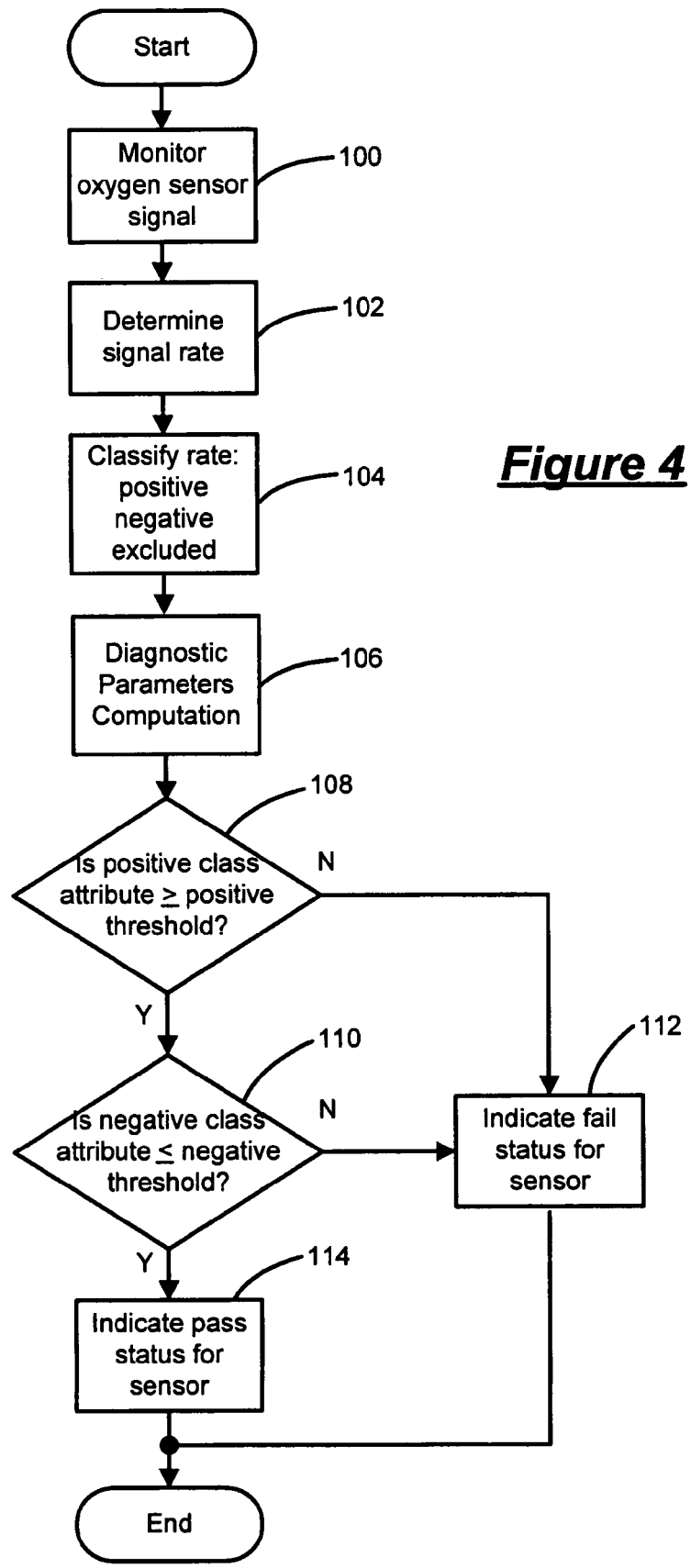
FIG. 4 is a flowchart illustrating the passive oxygen sensor diagnostic according to the present invention.

Referring now to FIG. 4, operation of the passive oxygen sensor diagnostic processed by the controller 16 will be described in detail. In step 100, a diagnostic algorithm monitors the oxygen sensor signal. The diagnostic algorithm determines the signal rate in step 102 and classifies the rate in step 104. The diagnostic parameters for the positive and negative classes are computed in step 106. In step 108, the diagnostic algorithm compares the positive class diagnostic parameters to the corresponding positive thresholds. These diagnostic parameters can include an average positive rate, a weighted moving average, a variance or any other function. If the positive class diagnostic parameters are greater than or equal to their corresponding thresholds, the diagnostic algorithm continues in step 110. Otherwise the algorithm continues in step 112. In step 110, the algorithm also determines whether the negative class diagnostic parameters are less than or equal to their corresponding negative thresholds. If step 110 is true, the algorithm continues in step 114. Otherwise, the algorithm continues in step 112.

In step 112, the diagnostic algorithm indicates a fail status of the sensor and the process ends. Fail status indication can occur in several manners. For example, the indication can occur as a fault that is stored in memory. Maintenance personnel are then made aware of the fault when servicing the engine system 10. The indication can also occur using visual or audible means such as a "check engine" light or tone. In step 114, the algorithm indicates a pass status of the sensor and then the process ends. A visual and/or audible indication need not occur upon when the sensor has a pass status. The controller 16 simply recognizes that the sensor is properly functioning.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. An engine exhaust sensor diagnostic system, comprising:
   an inlet oxygen sensor; and
   a controller that monitors a signal generated by said oxygen sensor, determines a rate of change of said signal, computes at least one diagnostic parameter based on said rate of change, and indicates a malfunction of said oxygen sensor if said diagnostic parameter is below a corresponding threshold, wherein said controller classifies said rate of change into one of a positive class, a negative class and an excluded class.

2. The system of claim 1 wherein said controller indicates proper function of said oxygen sensor if said diagnostic parameter is above said threshold.

3. The system of claim 1 wherein said excluded class rate of change is ignored.

4. The system of claim 1 wherein said threshold includes negative class thresholds and positive class thresholds and wherein a positive class diagnostic parameter is compared to said positive class thresholds and a negative class diagnostic parameter is compared to said negative class thresholds.

5. The system of claim 4 wherein said controller indicates a positive class malfunction if said positive class diagnostic parameters are below said positive class thresholds and indicates a negative class malfunction if said negative class diagnostic parameters are below said negative class thresholds.

6. The system of claim 4 wherein said controller indicates proper positive class function if said positive class diagnostic parameters are above said positive class thresholds and indicates proper negative class function if said negative class diagnostic parameters are above said negative class thresholds.

7. A method of monitoring operability of an oxygen sensor, comprising:
   monitoring a signal generated by said oxygen sensor;
   determining a rate of change of said signal;
   classifying said rate of change into one of a positive class, a negative class and an excluded class;
   computing diagnostic parameters based on said rate of change; and indicating malfunction of said oxygen sensor if said diagnostic parameters are below corresponding thresholds.

8. The method of claim 7 further comprising indicating proper function of said oxygen sensor if said diagnostic parameters are above said thresholds.

9. The method of claim 7 wherein said rate of change classified in said excluded class is ignored.

10. The method of claim 7 wherein said thresholds include negative class thresholds and positive class thresholds and wherein negative class diagnostic parameters are compared to said negative class thresholds and positive class diagnostic parameters are compared to said positive class thresholds.

11. The method of claim 10 further comprising:
    indicating a positive class malfunction if said positive class diagnostic parameters are below said positive class thresholds; and
    indicating a negative class malfunction if said negative class diagnostic parameters are below said negative class thresholds.

12. The method of claim 10 further comprising:
    indicating proper positive class function if said positive class diagnostic parameters are above said positive class thresholds; and
    indicating proper negative class function if said negative class diagnostic parameters are above said negative class thresholds.

13. A method of diagnosing operability of a sensor, comprising:
    monitoring a signal generated by said sensor;
    determining a rate of change of said signal;
    classifying said rate of change in one of a positive class, a negative class and an excluded class;
    computing diagnostic parameters for each of said classes based on said rate of change;
    indicating malfunction of said sensor if said positive class diagnostic parameters are below positive class thresholds; and
    indicating malfunction of said sensor if said negative class diagnostic parameters are below negative class thresholds.

14. The method of claim 13 wherein said excluded class rate of change is ignored.

15. The method of claim 13 further comprising:
    indicating proper positive class function if said positive class diagnostic parameters are above said positive class thresholds; and
    indicating proper negative class function if said negative class diagnostic parameters are above said negative class thresholds.

* * * * *